United States Patent
DelPrato et al.

(10) Patent No.: US 7,375,141 B2
(45) Date of Patent: May 20, 2008

(54) SOLUBLE CAROB

(75) Inventors: François DelPrato, St-Ouen l'Aumone (FR); Karl Heinrich Oskar Tiefenthaler, Kreuzlingen (CH); Eric Goron, Kreuzlingen (CH); Sophie Vaslin, Saint-Cloud (FR)

(73) Assignee: Danisco A/S (DK)

( * ) Notice: Subject to any disclaimer, the term of this patent is extended or adjusted under 35 U.S.C. 154(b) by 14 days.

(21) Appl. No.: 10/311,579

(22) PCT Filed: Jun. 12, 2001

(86) PCT No.: PCT/FR01/01809

§ 371 (c)(1),
(2), (4) Date: Jul. 17, 2003

(87) PCT Pub. No.: WO01/98369

PCT Pub. Date: Dec. 27, 2001

(65) Prior Publication Data

US 2004/0014822 A1    Jan. 22, 2004

(30) Foreign Application Priority Data

Jun. 19, 2000  (FR)  ................................. 00 07802

(51) Int. Cl.
*A23L 1/05* (2006.01)
*B01J 13/00* (2006.01)
*B01J 2/00* (2006.01)
*C08J 3/12* (2006.01)

(52) U.S. Cl. ........................ 516/107; 426/578; 516/928
(58) Field of Classification Search ................. 516/107
See application file for complete search history.

(56) References Cited

U.S. PATENT DOCUMENTS

| | | | | |
|---|---|---|---|---|
| 3,855,149 | A | | 12/1974 | Bielskis .................... 252/363.5 |
| 3,901,874 | A | * | 8/1975 | Hill ................................ 536/2 |
| 5,498,436 | A | * | 3/1996 | Modliszewski et al. ..... 426/573 |
| 5,633,030 | A | * | 5/1997 | Marrs et al. ................. 426/573 |
| 5,861,178 | A | * | 1/1999 | Burgin ........................ 424/499 |
| 6,086,904 | A | * | 7/2000 | Crawford .................... 424/405 |

OTHER PUBLICATIONS

International Search Report.

* cited by examiner

*Primary Examiner*—Randy Gulakowski
*Assistant Examiner*—Timothy J. Kugel
(74) *Attorney, Agent, or Firm*—Fay Sharpe LLP

(57) ABSTRACT

The invention concerns a gum carob with average mole weight (Mw) ranging between $2.5 \cdot 10^5$ and $1.5 \cdot 10^6$ g/mol and whereof at least 60 wt. % of said gum is soluble in an aqueous medium at a temperature not higher than 60° C.

16 Claims, No Drawings

SOLUBLE CAROB

This application is an application under 35 U.S.C. Section 371 of International Application Number PCT/FR01/01809 filed on Jun. 12, 2001.

The present invention relates to a carob bean gum (or locust bean gum) having a weight-average molecular mass ($\overline{M}_w$) of between $2.5 \times 10^5$ and $1.5 \times 10^6$ g/mol, at least 60% by weight of said gum being soluble in an aqueous medium at a temperature equal to or less than 60° C., to its method of preparation and to its use.

It also relates to a gelling composition comprising said carob bean gum and at least one hydrocolloid.

Various industries, such as the cosmetics, dyeing, food, oil and cleaning products industries, seek texture agents that modify the Theological properties of liquid phases, especially aqueous phases.

The rheology of aqueous phases is usually modified by glucide derivatives of plant or animal origin.

The choice of these glucide derivatives depends, for example, on their cost, their availability, the conditions under which they may be used and the types of compounds in which they may be suitable.

Thus, galactomannans, which are nonionic polysaccharides extracted from the albumen of seeds of leguminous plants of which they constitute the storage carbohydrate, are often employed as texture agents.

Among galactomannans most often employed, mention may be made of carob bean gum. This is extracted from the seeds of the carob tree (*Ceratonia siliqua* L.) which is a tree with persistent foliage originally from Syria and Asia Minor, but cultivated along the entire Mediterranean littoral.

Carob bean gum is composed of a main chain consisting of D-mannopyranose units linked in the β(1-4) position, carrying side branches consisting of a single D-galactopyranose unit in the α(1-6) position.

Carob bean gum is in general known for its texturing properties and more particularly for its thickening and stabilizing properties.

It is more particularly beneficial as, because of its nature, it is compatible with other compounds, especially hydrocolloids, and therefore can be used in combination with these to produce synergistic effects in terms of texture. For example, in combination with xanthan gum or carragheenans, gels of different strength and greater or lesser elastic consistency may be obtained.

However, in aqueous medium, native carob bean gum exhibits satisfactory solubility, that is to say greater than 60% by weight of the gum, only at temperatures above 80° C.

Thus, for practical and economic reasons, industrial concerns are currently seeking more and more to replace native carob bean gum with carob bean gums that have better solubility at temperatures below the usual temperatures for dissolving native carob bean gums.

The object of the present invention is to provide a carob bean gum having properties similar to those of native carobs (for example in terms of texturing, compatibility with other compounds, etc.) and good solubility at temperatures well below the usual temperatures for dissolving native carob bean gums.

The object of the invention is also to provide a carob bean gum which, at a constant concentration, allows a variable viscosity range to be achieved.

For this purpose, one subject of the present invention is a carob bean gum having a weight-average molecular mass ($\overline{M}_w$) of between $2.5 \times 10^5$ and $1.5 \times 10^6$ g/mol, at least 60% by weight of said gum being soluble in an aqueous medium at a temperature equal to or less than 60° C.

Another subject of the invention is a method of preparing the carob bean gum of the above type.

Yet another subject of the invention is gelling compositions comprising the carob bean gum of the above type and at least one hydrocolloid.

Finally, the invention relates to food formulations comprising the abovementioned gelling compositions.

Within the context of the present invention, the expression "solubility in an aqueous medium at a temperature equal to or less than 60° C." means that at a temperature equal to or less than 60° C., in an aqueous medium, the carob bean gum develops 60% of the viscosity that it would have developed if it had been dissolved at temperatures above 80° C.

Within the meaning of the invention, "aqueous medium" denotes a medium which consists partly of water.

Thus, the subject of the invention is firstly a carob bean gum having a weight-average molecular mass ($\overline{M}_w$) of between $2.5 \times 10^5$ and $1.5 \times 10^6$ g/mol, at least 60% by weight of said gum being soluble in an aqueous medium at a temperature equal to or less than 60° C.

Under these temperature conditions, the solubility of the gum according to the invention may advantageously be at least 70% by weight, and preferably be at least 80% by weight, of said gum.

These solubility levels—that is to say at least 60% by weight, advantageously at least 70% by weight and preferably at least 80% by weight of the gum—may be achieved more particularly at temperature one less than 60° C., advantageously between 10° C. and 45° C. and preferably between 15° C. and 30° C.

In a preferred embodiment of the invention, these solubility levels are achieved at a temperature that may vary from 20° C. to 25° C.

The weight-average molecular mass ($\overline{M}_w$) of the gum according to the invention is advantageously between $2.5 \times 10^5$ and $1 \times 10^6$ g/mol and preferably between $2.5 \times 10^5$ and $6 \times 10^5$ g/mol.

It may be measured by gel permeation chromatography (GPC). In this case, standard synthetic polymer solutions are used for the calibration.

It may also be determined by light scattering.

The viscosity measurement may also give information about the weight-average molecular mass ($\overline{M}_w$). Thus at 25° C. a 1% aqueous solution of the carob bean gum according to the invention has a viscosity of between 15 and 2000 mPa·s (measured at 20 rpm). The viscosity of such a solution is preferably between 15 and 1000 mPa·s.

The viscosity may be measured using a BROOKFIELD DV-III viscometer at 25° C. and 20 rpm.

The weight-average molecular mass ($\overline{M}_w$) of the carob bean gum according to the invention is such that its intrinsic viscosity [η] is greater than 2.3 dl/g.

The relationship between the intrinsic viscosity [η] and the weight-average molecular mass ($\overline{M}_w$) can be obtained in the following manner (A. Sabater de Sabates, 1979, Doctoral Thesis, University of Orsay, ENSIA, Massy, France):

$$[\eta] = 1.24 \times 10^{-4} \times \overline{M}_w^{0.8}$$

This viscosity is measured by means of a U-shaped viscometer of the Ubbelhode type.

The D-mannopyranose/D-galactopyranose mass ratio (M/G) of the carob according to the invention is between 1 and 5, preferably between 2 and 4. Knowing this ratio constitutes one of the means of characterizing the specimen, although it provides no information about the statistical distribution of the D-galactopyranose branches along the main chain.

The carob bean gum having the aforementioned characteristics is obtained by reducing the weight-average molecular mass ($\overline{M}_w$) of the native gum. This reduction is in general obtained by scission of the glycosic bonds for the purpose of producing shorter chains which are substantially identical, from the chemical standpoint, to the native gum.

Reducing the weight-average molecular mass ($\overline{M}_w$) gives the gum certain advantages. For example, it makes it possible to obtain a carob whose texturing properties, in particular its thickening and stabilizing properties, may be adjusted. Furthermore, it allows a carob bean gum to be obtained which is capable of forming pseudo-gels and/or having emulsifying properties, hence distinguishing it from the native gum.

Another aspect of the invention is the method of preparing the carob bean gum as described above.

This method comprises the following steps:
(i) the endosperm of the carob bean gum is hydrated;
(ii) the hydrated endosperm is simultaneously dried and ground; and
(iii) after step (ii), the weight-average molecular mass of the carob is reduced by depolymerizing the latter.

In step (i), the hydration of the carob bean gum endosperm is carried out for a time long enough to achieve a degree of hydration of between 50 and 90%.

The degree of hydration may be calculated, for example, by simply measuring the solids content of the endosperm.

After step (ii), the carob is in the form of a powder with a water content which is advantageously between 6 and 12%.

The particle size of this powder may vary depending on the operating conditions. For example, it may vary from 20 to 200 µm.

The particle size may be measured by laser diffraction, for example using a Malvern Mastersizer® 2000 laser particle size analyzer.

The drying/grinding operation is more particularly carried out at a temperature of between 30° C. and 90° C.

This operation may be carried out in any type of apparatus for simultaneous grinding and drying, such as for example a hammer mill or needle mill.

The depolymerization of the carob may be carried out by oxidation, by an enzymatic process, or by acid hydrolysis, under the effect of high temperature and pressure and in the presence of an oxidizing agent, or by physical treatment such as, for example, by exposure to gamma-type radiation.

Advantageously, the depolymerization is carried out by oxidation. The oxidation is preferably carried out in an alkaline medium in the presence of an agent of the type belonging to the family of peroxides, such as peracetic acid, $H_2O_2$, etc.

The depolymerization reaction time depends on the final weight-average molecular mass desired.

The depolymerization may be carried out in a reactor provided with a mixing system suitable for handling fine powder, that is to say powder with a particle size of around 20 to 200 µm, so as to prevent the formation of crumbs. As nonlimiting examples, mention may be made of LÖDIGE-type reactors, and ribbon mixers.

After depolymerization, if necessary, the excess alkalinity may be neutralized by adding, for example, ammonium hydroxide or an acid, such as acetic acid, citric acid, phosphoric acid or sulfuric acid.

The depolymerized carob may then be dried. This drying may be carried out in any type of apparatus that avoids the formation of agglomerates. For example, a Turbosphere, a needle mill or a flash dryer may be used.

The final carob bean gum is preferably in the form of a powder. Its water content is advantageously between 6 and 12%.

The steps may be carried out in any order. However, they are preferably carried out in the order indicated above.

The carob bean gum according to the invention have physico-chemical characteristics compatible with the definitions of the carob bean gum that are described in "*Food Chemical Codex*", 4th edition, page 768 and in European Union (EU) Directive No. 98/86/CE of Nov. 11, 1998.

The carob bean gum of the invention may be used as a texture agent, especially as thickeners, stabilizers, gelling agents (capable of forming pseudo-gels) and/or emulsifiers in the field of cosmetics, the dyeing and food industries, the oil industry and the field of cleaning products.

Said gum is intended more particularly for the food field.

In combination with other compounds, especially hydrocolloids, the carob bean gum of the present invention may form a gel whose physical properties (melting point, gel strength, etc.) may be controlled.

At this stage, it is appropriate to define the term "gel". Within the context of the present invention, by the term "gel" is meant a pseudo-solid (behavior approaching that of a solid) resulting from the at least partial combination of polysaccharide chains dispersed in a liquid. Within a range of stressing frequencies ω, pseudo-solid gels are in general characterized as regards their solid component by an elastic modulus $G'(\omega)$, also called the storage modulus, and as regards their liquid or viscous component by a viscous modulus $G''(\omega)$ also called the loss modulus.

The mechanical quantities $G'(\omega)$ and $G''(\omega)$ may be measured using an imposed-strain rheometer operating in oscillatory mode. As an indicative and nonlimiting example, mention may be made of a Rheo-Fluid Spectrometer® rheometer.

$G'(\omega)$ and $G''(\omega)$ may also be measured using an imposed-stress rheometer operating in oscillatory mode. As an indicative example, mention may be made of a AR1000® rheometer (from TA Instruments).

The principle of the measurement consists in determining firstly the range of reversible mechanical strain in which the response of the gel to the mechanical stress as a function of said strain is linear. Secondly, the gel is subjected to a fixed value of mechanical strain within the linear range determined above. The rheometer then performs an ω frequency sweep.

That stress response of the gel which is in phase with the strain enables the elastic modulus $G'(\omega)$ to be obtained. $G'(\omega)$ corresponds to the energy stored by the gel in elastic form, this energy being recoverable.

That stress response of the gel which is out of phase by an angle of 90° with the strain enables the viscous modulus $G''(\omega)$ to be obtained. $G''(\omega)$ corresponds to the energy dissipated by viscous flow, this energy being nonrecoverable.

A gel is called a true gel when, over the entire range of swept stressing frequencies (ω), the G'/G" ratio is greater than or equal to 10 and when the value of $G'(\omega)$ is greater than or equal to 10 Pa.

Likewise, a gel is called a pseudo-gel when, over the entire range of swept stressing frequencies (ω), the G'/G" ratio is greater than or equal to 5 and when the value of G'(ω) is greater than or equal to 1 Pa.

Another aspect of the present invention relates to gelling compositions comprising carob bean gum according to the invention with at least one hydrocolloid.

Completely unexpectedly, it has been found that the carob bean gum of the invention by itself or in combination with at least one hydrocolloid can result in a pseudo-gel at a temperature equal to or less than 60° C. It has also been found that, as in the case of the native carob bean gum, the combination of the carob of the invention with at least one hydrocolloid can give true gels by heating to a temperature equal to or greater than 80° C.

Among hydrocolloids, mention may be made by way of nonlimiting example of xanthan gum, carragheenans, agar, Danish agar, and gellan gum. Preferably, the hydrocolloid is xanthan gum.

In these compositions, the mass ratio of carob bean gum as defined above to the hydrocolloid(s) is(are) chosen between 5/95 and 95/5, advantageously between 20/80 and 80/20 and preferably between 40/60 and 60/40.

According to one embodiment of the invention, this mass ratio is 50/50.

These compositions may be obtained by simple mixing of the components, namely the carob and the hydrocolloid or hydrocolloids. The components may be mixed in the form of powder and then dissolved. They may also be mixed in the form of solutions. It may also be envisioned to add one of the components in powder form to the other component, which is in solution. In the latter case, it is important to avoid the formation of agglomerates during mixing.

Furthermore, the invention relates to a method of gelling an aqueous phase, characterized in that a pseudo-gel is formed by the addition of a gelling composition as defined above to said phase, at a temperature equal to or less than 60° C., more particularly less than 60° C., advantageously between 10° C. and 45° C. and preferably between 15° C. and 30° C., and after a sufficient rest time.

In a preferred embodiment of the invention, the addition of the gelling composition may be carried out at a temperature that may vary from 20° C. to 25° C.

It should be noted that in the preferred embodiment of the invention, the addition of the gelling composition and the formation of the pseudo-gel take place at a temperature that may vary from 20° C. to 25° C.

The invention also extends to the method of gelling an aqueous phase, characterized in that a true gel is formed by the addition of a gelling composition as defined above to said phase, at a temperature equal to or greater than 80° C., and [lacuna] a sufficient rest time.

Given that, to form a true gel, the addition of the gelling composition to the aqueous phase will take place at temperatures equal to or greater than 80° C., a cooling step will possibly be necessary.

A person skilled in the art is capable of determining the suitable rest time depending on the desired G'(ω) and G"(ω) values.

Thus, it has been found that, for example, 1% weight/weight solutions of the gelling composition in distilled water at 25° C., at a frequency of 1 Hz, lead to G'(ω) values of between 1 and 1000 Pa, preferably between 10 and 1000 Pa, with a G'/G" ratio of greater than 5.

The amount of the gelling composition that can be used will depend on the aqueous phase to be gelled. This amount may represent from 0.01 to 10%, advantageously from 0.5 to 2% and preferably from 0.8 to 1.5% by weight, of the gelled phase.

It does not matter whether the gelling composition is introduced in the form of a solid or in the form of an aqueous solution.

These gelling compositions may be used in the oil, agrochemical, food, paper and textile industries, as well as in paints and domestic or industrial cleaning agents.

More particularly, the gelling compositions are intended for food formulations.

Among the food formulations in which the use of such compositions are suitable, mention may be made, for example, of compositions of the following types: jellies, custards, cup custards, aspic, cold jellied poultry, bavaroises, yogurts, ice creams, sorbets, crèmes brûlées, drinks, etc.

Specific but nonlimiting examples of the invention will now be given.

EXAMPLES

In the examples that follow, the intrinsic viscosity and the weight-average molecular mass ($\overline{M}_w$) are determined in the following manner:

Measurement of the Intrinsic Viscosity

A 1% weight/weight solution of the carob according to the invention is prepared by vigorous stirring in demineralized water. The solution is then left to stand at about 25° C. for 24 h. By centrifuging for 1 h at 14 000 rpm, the supernatant liquid is recovered and filtered on glass wool. This mother liquor is then used to prepare solutions of lower concentrations by dilution in demineralized water.

The reduced viscosities, and then specific viscosities, are then calculated at 25° C. with a U-shaped viscometer of the Ubbelhode type by measuring the drop times.

Finally, the intrinsic viscosities [η] are determined by extrapolation to zero concentration:
- either by the Huggins method, by plotting the "specific viscosity/concentration" curve as a function of concentration;
- or by the Kraemer method, by plotting the "natural logarithm of the reduced viscosity/concentration" curve as a function of concentration. The two methods give the same result.

Measurement of the Weight-Average Molecular Mass

The weight-average molecular mass is determined by gel permeation chromatography using polyethylene oxide standard solutions as calibration standards.

Example 1

Preparation of a Carob Bean Gum According to the Invention

By following steps (i) to (iii) of the process described in the text (depolymerization by alkaline oxidation in the presence of sodium hydroxide NaOH and hydrogen peroxide $H_2O_2$; neutralization with acetic acid $CH_3CO_2H$; reaction time of 100 minutes at 70° C.) in the order indicated, a carob bean gum having the following characteristics was obtained:
- water content: 11.2%;
- Brookfield viscosity at 25° C. and 20 rpm of a 2% weight/weight solution in demineralized water:
  - after 24 h and dissolved at 25° C.: 150 mPa·s, after 24 h and dissolved at 80° C.: 190 mPa·s, hence a solubility of 79%;

intrinsic viscosity: [Λ]=3.7 dl/g;

weight-average molecular mass: $\overline{M}_w$=4.5×10$^5$ g/mol; and equilibrium surface tension of a 0.5% weight/weight solution in distilled water: γ=39 mN/m (measured at 25° C. by means of a drop volume tensiometer of the LAUDA TVT 1 type).

Example 2 (Comparative Example)

Preparation of Only Depolymerized Carob Bean Gum

By carrying out only step (iii) of depolymerizing a native carob bean gum, without passing through steps (i) and (ii) prior to depolymerization, a carob bean gum having a viscosity, after being dissolved at a temperature greater than or equal to 80° C., similar to the carob bean gum of example 1 was obtained. However, the level of solubility of this gum was substantially less than 60% by weight. This gum had the following characteristics:

the BROOKFIELD viscosity at 25° C. and 20 rpm of a 2% weight/weight solution in demineralized water:
  after 24 h and dissolved at 25° C.: 57 mPa·s,
  after 24 h and dissolved at 80° C.: 243 mPa·s, hence a solubility of 23%.

Example 3

Gelling Composition According to the Invention

The gelling composition of example 3 was prepared by mixing, in a 50/50 weight ratio, the following two powders: the carob bean gum of example 1 and xanthan gum (RHODIGEL™ 200 sold by Rhodia).

After dissolving this gelling composition by vigorous stirring for 10 minutes in an aqueous medium at 25° C. and after a rest time of 24 h at a temperature of around 25° C., pseudo-gels having the following characteristics were obtained:

for a total concentration of gelling composition of 1% weight/weight in demineralized water, the moduli G'(ω) and G"(ω) were 40 and 8 Pa, respectively;

for a total concentration of gelling composition of 1% weight/weight in skimmed milk (10% weight/weight solution of powdered skimmed milk in demineralized water), the moduli G'(ω) and G"(ω) were 100 and 20 Pa, respectively.

For the same gelling composition, after being dissolved by vigorous stirring for 10 minutes in an aqueous medium at a temperature greater than or equal to 80° C., and after a rest time of 24 h at a temperature of around 25° C., true gels were obtained with the following characteristics (total concentration of gelling composition of 1% weight/weight in a 1% weight/weight KCl solution):

the moduli G'(ω) and G"(ω) were 140 and 7 Pa, respectively;

the gelling and melting temperatures were 54° C. and 56° C. respectively (these temperatures were determined at the point of intersection of the G' and G" versus temperature curves; variation at −2° C./min in the case of gelling and at +2° C./min in the case of melting, within the reversible mechanical deformation range of the gel, at a frequency of 1 Hz); and the strength of the gel for a depth of penetration of 10 mm was 80 g/cm$^2$ (determined using a texturometer of the TA-XT2® type for a rate of penetration of the piston of 0.5 mm/s; cylinder of 1 cm$^2$ cross section).

As a comparison, by following the same operating method as described above (by dissolving the powder mixture with vigorous stirring for 10 minutes in an aqueous medium at a temperature equal to or greater than 80° C.; rest time of 24 h at a temperature of around 25° C.), true gels were obtained with a native carob (MEYPRO-FLEUR™ 200, sold by Meyhall AG)/xanthan gum (RHODIGEL™ 200, sold by Rhodia) mixture (50/50 weight ratio), said true gels having the following characteristics (total concentration of gums of 1%. weight/weight in a 1% weight/weight KCl solution):

the moduli G'(ω) and G"(ω) were 200 and 10 Pa, respectively;

the gelling and melting temperatures were 62° C. and 67° C., respectively; and the strength of the gel for a depth of penetration of 10 mm was 83 g/cm$^2$.

It may therefore be seen that the interaction between the carob bean gum of the invention and the xanthan gum is greatly favored compared with the native carob bean gum (this is because, for the same amount of carob bean gum according to example 1 and of the native carob bean gum, the same gel strength is obtained, whereas the BROOKFIELD viscosity developed by the native carob bean gum is appreciably higher: 3000 mPa·s at a concentration of 1% weight/weight; dissolved at a temperature above 80° C.; BROOKFIELD viscosity measured at 25° C. and 20 rpm).

Example 4

Use of a Gelling Composition in Custard-Type Food Formulations

Vanilla Custard

| Ingredients | |
|---|---|
| Sugar | 12.0% |
| Gelling composition[1] | 0.80% |
| Vanilla flavoring | 0.05% |
| Coloring agent | 0.05% |
| NaCl | 0.02% |
| Semiskimmed milk | the balance to 100% |

Gelling agent[1] (this was the gelling composition of example 3), namely a mixture of the carob bean gum of example 1 with xanthan gum (RHODIGEL ™ 200, sold by Rhodia) in a 50/50 weight ratio.

Recipe

Mix the gelling composition with the other dry ingredients;

Heat the milk to 85° C.;

Introduce the powder mixture and stir at 85° C. for 15 minutes at 1000 rpm;

Leave to cool and stand overnight in a refrigerator at 4° C.=6° C.

Characterization of the Custard

An elastic gel was obtained, with a moderate gel strength (30 g/cm$^2$ at 10 mm) and suitable organoleptic qualities.

If in the gelling composition the carob bean gum of example 1 were to be replaced with native carob bean gum, a firmer custard, less pleasant in one's mouth, was obtained.

The invention claimed is:

1. A method of preparing a carob bean gum comprising the steps of:

(i) hydrating the endosperm of the carob bean gum;
(ii) simultaneously drying and grinding the hydrated endosperm obtained in step (i); and, then,
(iii) reducing the weight-average molecular mass of the carob by depolymerising the latter,
wherein the carob bean gum obtained has a weight-average molecular mass of between $2.5 \times 10^5$ and $1.5 \times 10^6$ g/mol, at least 60% of said gum being soluble in an aqueous medium at less than 60° C.

2. A gelling composition comprising carob bean gum obtained according to claim 1 with at least one hydrocolloid.

3. The gelling composition as claimed in claim 2, wherein the mass ratio is between 40/60 and 60/40.

4. The gelling composition as claimed in claim 3, wherein the mass ratio of the carob bean gum to the hydrocolloid is 50/50.

5. The gelling composition as claimed in claim 2, wherein the hydrocolloid is xanthan gum, carragheenans, agar, Danish agar, or gellan gum.

6. The gelling composition as claimed claim 2, having a mass ratio of carob bean gum to the hydrocolloid of between 5/95 and 95/5.

7. An oil, agrochemical, food paper, textile, paint, domestic or industrial cleaning agent, comprising a gelling composition as defined in claim 2.

8. Jellies, custards, cup custards, aspic, cold jellied poultry, bavaroises, yogurts, ice creams, sorbets, crèmes brûlées, comprising a gelling composition as defined in claim 2.

9. A method of gelling an aqueous phase, comprising the steps of:
a) forming a pseudo-gel by the addition of a gelling composition to said phase, said composition comprising a carob bean gum obtained according to claim 1, having a weight-average molecular mass of between $2.5 \times 10^5$ and $1.5 \times 10^6$ g/mol, at least 60% by weight of said gum being soluble in an aqueous medium at a temperature equal to or less than 60° C. and a hydrocolloid.

10. The method as claimed in claim 9, wherein step a) is carried out at a temperature varying from 20° C. to 25° C.

11. The method as claims in claim 1, wherein in step (i), the hydration of the carob bean gum endosperm is carried out for a time long enough to achieve a degree of hydration of between 50 and 90%.

12. The method as claimed in claim 1, wherein after step (ii), the carob is in the form of a powder with a water content of between 6 and 12%.

13. The method as claimed in claim 1, wherein the drying/grinding operation is carried out at a temperature of between 30° C. and 90° C.

14. The method as claimed in claim 1, wherein the depolymerization of step (iii) is carried out by oxidation.

15. A thickener, stabilizer, gelling agent or emulsifier, comprising a carob bean gum obtained according to claim 1.

16. A method of preparing a carob bean gum comprising the successive steps of:
(i) hydrating the endosperm of the carob bean gum;
(ii) simultaneously drying and grinding the hydrated endosperm obtained in step (i); and, then
(iii) depolymerizing the product obtained in step (ii) to a weight-average molecular mass of between $2.5 \times 10^5$ and $1.5 \times 10^6$ g/mol,
thereby at least 60% of said gum is soluble in an aqueous medium at less than 60° C.

* * * * *